(12) United States Patent
Srinivasan et al.

(10) Patent No.: US 7,946,990 B2
(45) Date of Patent: May 24, 2011

(54) ULTRASOUND COLOR FLOW IMAGING AT HIGH FRAME RATES

(75) Inventors: Seshadri Srinivasan, Mountain View, CA (US); Patrick J. Phillips, Sunnyvale, CA (US); Charles E. Bradley, Burlingame, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1634 days.

(21) Appl. No.: 11/242,162

(22) Filed: Sep. 30, 2005

(65) Prior Publication Data

US 2007/0078347 A1    Apr. 5, 2007

(51) Int. Cl.
    *A61B 8/00*    (2006.01)
    *A61B 8/14*    (2006.01)
(52) U.S. Cl. ......... 600/454; 600/437; 600/455; 600/465
(58) Field of Classification Search ................. 600/437, 600/441
    See application file for complete search history.

(56) References Cited

U.S. PATENT DOCUMENTS

| | | | |
|---|---|---|---|
| 4,534,357 A | 8/1985 | Powers | |
| 5,555,534 A | 9/1996 | Maslak et al. | |
| 5,581,517 A | 12/1996 | Gee et al. | |
| 5,623,928 A | 4/1997 | Wright et al. | |
| 5,675,554 A | 10/1997 | Cole et al. | |
| 5,685,308 A | 11/1997 | Wright et al. | |
| 5,891,040 A * | 4/1999 | Grenon et al. | 600/455 |
| 5,921,931 A * | 7/1999 | O'Donnell et al. | 600/441 |
| 5,921,932 A | 7/1999 | Wright et al. | |
| 5,938,611 A | 8/1999 | Muzilla et al. | |
| 6,159,153 A * | 12/2000 | Dubberstein et al. | 600/443 |
| 6,179,781 B1 | 1/2001 | Phillips | |
| 6,213,947 B1 * | 4/2001 | Phillips | 600/443 |
| 2004/0254467 A1 | 12/2004 | Jackson et al. | |

OTHER PUBLICATIONS

"Transmit Multibeam for Compounding Ultrasound Data," U.S. Appl. No. 11/099,866, filed Apr. 5, 2005, inventors: Kutay F. Ustuner, Anming He Cai, and Charles E. Bradley.

"Automatic Velocity Scale Identification for Medical Diagnostic Ultrasound," U.S. Appl. No. 11/202,676, filed Aug. 12, 2005, inventors: Seshadri Srinivasan, Bhaskar S. Ramamurthy, Ismayil M. Guracar, Patrick J. Phillips, and Rickard C. Loftman.

* cited by examiner

*Primary Examiner* — Unsu Jung
*Assistant Examiner* — Katherine L Fernandez

(57) ABSTRACT

A method is provided to improve the frame-rate in color-flow ultrasound imaging using simultaneous spatially-distinct transmit beams with one or more frequency bands per transmit beam. Pulses of different center frequencies are used simultaneously in different (lateral and/or elevational) directions, thereby reducing the scanning time and improving the frame-rates. Optionally, a multi-modal pulse is used, and flow is estimated separately for the different frequencies. The flow estimates for these pulses are appropriately combined to improve low-velocity sensitivity and to reduce aliasing. A flow sample count with two or more different pulse repetition intervals can be used to further improve low-flow sensitivity and minimize aliasing.

51 Claims, 6 Drawing Sheets

US 7,946,990 B2

ULTRASOUND COLOR FLOW IMAGING AT HIGH FRAME RATES

BACKGROUND

Color Doppler flow imaging is used in medical diagnostic ultrasound imaging systems to measure the flow velocity of fluid or tissue under examination. Because of the larger number of ultrasound pulses that need to be transmitted and received to estimate and display flow velocity, the frame rate is much lower than that of B-mode imaging. Accordingly, to display flow velocity in real-time along with a B-mode image, flow velocity is displayed in a "color box" that is smaller than the whole field of view of the B-mode image. There is, therefore, a need to improve the frame rate of color flow imaging. U.S. Pat. No. 6,159,153 describes systems and methods for improving frame rates in B-mode imaging by using multiple firing directions and multiple frequencies. However, these methods and systems are only directed to B-mode imaging and not to color flow imaging.

SUMMARY

The present invention is defined by the following claims, and nothing in this section should be taken as a limitation on those claims.

By way of introduction, the preferred embodiments described below provide a method and system for ultrasound color flow imaging at high frame rates. In one preferred embodiment, a plurality of transmit ultrasound beams are generated, with each beam comprising a different center frequency and being directed at a different spatial location. A plurality of receive ultrasound beams responsive to the plurality of transmit ultrasound beams are received, and flow velocity is estimated. In another preferred embodiment, simultaneous spatially distinct transmit beams with multiple frequency bands per transmit beam are generated, flow velocity is estimated for each frequency band, and the flow velocity estimates are combined at each spatial location. Other preferred embodiments are provided, and each of the preferred embodiments described herein can be used alone or in combination with one another.

The preferred embodiments will now be described with reference to the attached drawings.

DETAILED DESCRIPTION OF THE PRESENTLY PREFERRED EMBODIMENTS

By way of overview, the preferred embodiments described below relate to improving frame rate in color flow ultrasound imaging. The following section presents an overview of the system, and the subsequent section describes techniques for improving frame rate in color flow ultrasound imaging. One disclosed technique uses simultaneous spatially distinct transmit beams with multiple frequency bands per transmit beam. In addition to describing techniques that can be used to realize frame rate improvements, that section also describes techniques that can be used to improve the robustness of color flow imaging.

System Overview

Figure 1:
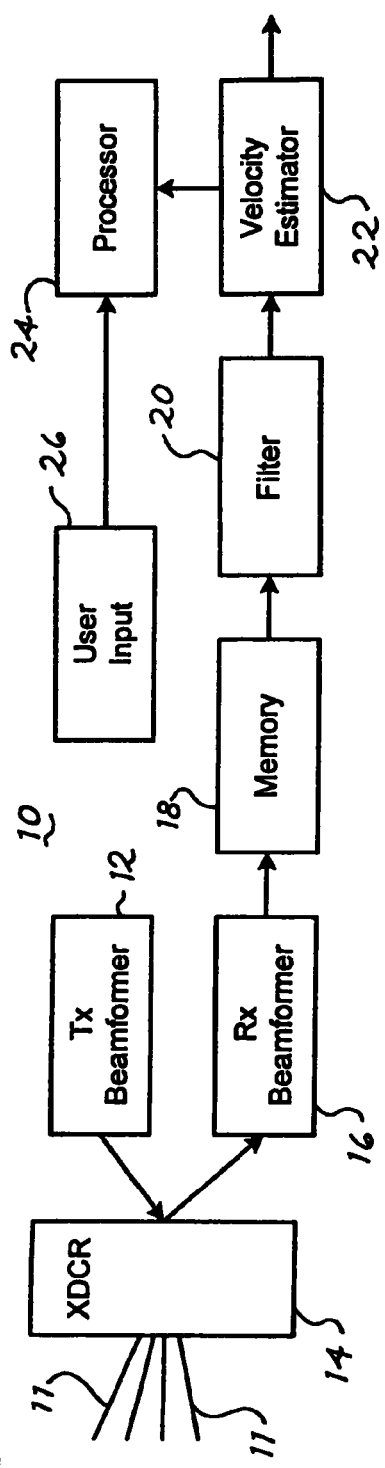
FIG. 1 is a block diagram of a medical diagnostic ultrasound imaging system of a preferred embodiment.

Turning now to the drawings, FIG. 1 is a block diagram of a system 10 of a preferred embodiment. The system 10 includes a transmit beamformer 12, a transducer 14, a receive beamformer 16, a memory 18, a filter 20, a velocity estimator 22, a processor 24 and a user input 26. Additional, different or fewer components may be provided. For example, a scan converter and display can be provided. In one embodiment, the system 10 is a medical diagnostic ultrasound system. In an alternative embodiment, the system 10 is a computer or workstation. In yet another embodiment, the velocity estimator 22 is part of a medical diagnostic ultrasound system or other medical imaging system, and the processor 24 is part of a separate work station or remote system.

The transmit beamformer 12 is shown separate from the receive beamformer 16. Alternatively, the transmit and receive beamformers 12, 16 may be provided with some or all components in common. Operating together or alone, the transmit and receive beamformers 12, 16 form beams of acoustic energy for scanning a one, two or three dimensional region. One or more scan lines 11 are scanned. Vector®, sector, linear or other scan formats may be used. A single receive beam can be generated for each transmit beam. Alternatively, two or more receive beams can be generated for each transmit beam. Data representing scan lines may be synthesized from coherent receive beam data, such as disclosed in U.S. Pat. No. 5,623,928, the disclosure of which is incorporated herein by reference. Fully populated control data sets for any of the transmit or receive beamformer parameters discussed herein are provided. Alternatively, sparse sets are used for real-time calculation of the control data, such as disclosed in U.S. Pat. No. 5,581,517, the disclosure of which is incorporated herein by reference.

The transmit beamformer 12 is preferably a processor, delay, filter, waveform generator, memory, phase rotator, digital-to-analog converter, amplifier, combinations thereof or any other now known or later developed transmit beamformer components. In one embodiment, the transmit beamformer 12 is preferably the transmit beamformer disclosed in U.S. Pat. No. 5,675,554, the disclosure of which is incorporated herein by reference. The transmit beamformer 12 digitally generates envelope samples. Using filtering, delays, phase rotation, digital-to-analog conversion and amplification, the desired transmit waveform is generated. Other waveform generators may be used, such as switching pulsers or waveform memories.

The transmit beamformer 12 is preferably configured as a plurality of channels for generating electrical signals of a transmit waveform for each element of a transmit aperture on the transducer 14. The waveforms are unipolar, bipolar, stepped, sinusoidal or other waveforms of a desired center frequency or frequency band with one, multiple or fractional number of cycles. The waveforms have relative delay and/or phasing and amplitude for focusing the acoustic energy. The transmit beamformer 12 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles and combinations thereof. A scan line focus is generated based on these beamforming parameters.

The transducer 14 is preferably an array of a plurality of elements. The elements are preferably piezoelectric or capacitive membrane elements. The array is configured as a one-dimensional array, a two-dimensional array, a 1.5D array, a 1.25D array, a 1.75D array, an annular array, a multidimensional array, combinations thereof or any other now known or later developed array. The transducer elements transduce between acoustic and electric energies. The transducer 14 connects with the transmit beamformer 12 and the receive beamformer 16 through a transmit/receive switch, but separate connections may be used in other embodiments.

The receive beamformer 16 is preferably a preamplifier, filter, phase rotator, delay, summer, base band filter, processor, buffers, memory, combinations thereof or other now known or later developed receive beamformer components. In one embodiment, the receive beamformer is one disclosed in U.S. Pat. Nos. 5,555,534, 5,921,932 and 5,685,308, the disclosures of which are incorporated herein by reference. Other analog or digital receive beamformers may be used. The receive beamformer 16 is preferably configured into a plurality of channels for receiving electrical signals representing echoes or acoustic energy impinging on the transducer 14. A channel from each of the elements of the receive aperture within the transducer 14 connects to an amplifier and/or delay. An analog-to-digital converter digitizes the amplified echo signal. The digital radio frequency received data is demodulated to a base band frequency. Any receive delays, such as dynamic receive delays, and/or phase rotations are then applied by the amplifier and/or delay. A digital or analog summer combines data from different channels of the receive aperture to form one or a plurality of receive beams. The summer is a single summer or cascaded summer. In one embodiment, the beamform summer is operable to sum in-phase and quadrature channel data in a complex manner such that phase information is maintained for the formed beam. Alternatively, the beamform summer sums data amplitudes or intensities without maintaining the phase information.

A control processor controls the various beamforming parameters for receive beamformation. The values provided for the beamformer parameters for the receive beamformer 16 are the same or different than the transmit beamformer 12. For example, an aberration or clutter correction applied for receive beam formation is different than an aberration correction provided for transmit beam formation due to differences in signal amplitude.

The receive beamformer 16 is preferably operable to form receive beams in response to the transmit beams. For example, the receive beamformer 16 receives one or two receive beams in response to each transmit beam. The receive beams are collinear, parallel and offset or nonparallel with the corresponding transmit beams. A substantially same scan line accounts for patient movement or the use of overlapping beams.

The receive beamformer 16 outputs image data, data representing different spatial locations of a scanned region. The image data is coherent (i.e., maintained phase information) or incoherent. The data may be formed by processing received data, such as synthesizing scan lines (i.e., coherent combination), or other processes for generating data used to form an image from received information. For example, inter-beam phase correction is applied to one or more beams, and then the phase corrected beams are combined through a coherent (i.e., phase sensitive) filter to form synthesized ultrasound lines and/or interpolated between beams to form new ultrasound lines. Once the channel data is beamformed or otherwise combined to represent spatial locations along the scan lines 11, the data is converted from the channel domain to the image data domain.

For imaging motion, such as tissue motion or fluid flow, multiple transmissions and corresponding receptions are performed for a substantially same spatial location. Phase changes between the different receive events indicate the velocity of the tissue or fluid. A flow sample group corresponds to multiple transmissions for each of a plurality of scan lines 11. The scan lines 11 may be sparsely sampled, such as scanning every eighth, tenth or sixteenth scan line 11 multiple times for each flow sample grouping. The number of times a substantially same spatial location, such as a scan line 11, is scanned within a flow sample group is the flow sample count. The transmissions for different scan lines 11, different flow sample groupings or different types of imaging may be interleaved. The amount of time between transmissions to a substantially same scan line 11 within the flow sample count is the pulse repetition interval or pulse repetition frequency. Pulse repetition interval is used herein, but includes the pulse repetition frequency.

The memory 18 is video random access memory, random access memory, removable media (e.g. diskette or compact disc), hard drive, database, corner turning memory or other memory device for storing data or video information. In one embodiment, the memory 18 is a corner turning memory of a flow, color or velocity path. The memory 18 is operable to store signals responsive to multiple transmissions along a substantially same scan line. The memory 22 is operable to store ultrasound data formatted in an acoustic grid, a Cartesian grid, both a Cartesian coordinate grid and an acoustic grid, or ultrasound data representing a volume in a 3D grid.

The filter 20 is preferably a clutter filter, finite impulse response filter, infinite impulse response filter, analog filter, digital filter, combinations thereof or other now known or later developed filter. In one embodiment, the filter 20 includes a mixer to shift signals to base band and a programmable low pass filter response for removing or minimizing information at frequencies away from the base band. In other embodiments, the filter 20 is a low pass, high pass or band pass filter. The filter 20 identifies velocity information from slower moving tissue as opposed to fluids or alternatively reduce the influence of data from tissue while maintaining velocity information from fluids. The filter 20 has a set response or may be programmed, such as altering operation as a function of signal feedback or other adaptive process. In yet another embodiment, the memory 18 and/or the filter 20 are part of the velocity estimator 22.

The velocity estimator 22 is preferably a Doppler processor or cross-correlation processor for estimating velocity. In one embodiment, the velocity estimator 22 allows time division multiplexing for determining multiple estimates of velocity substantially simultaneously. Parallel processing or sequential processing to obtain two or more velocity estimates representing a same spatial location may be used. In alternative embodiments, another device now known or later developed for estimating velocities from any or various input data may be provided. The velocity estimator 22 receives a plurality of signals associated with a substantially same location at different times and estimates a Doppler shift frequency, based on a change or an average change in phase between consecutive signals from the same location. A flow velocity estimate is calculated from the Doppler shift frequency. Alternatively, the Doppler shift frequency is itself used as an estimate of the velocity. The velocity estimator 12 outputs velocity data that may include aliased information or velocities. Where an actual velocity is outside of the velocity scale (i.e. PRI) or range as a function of the Nyquist sampling frequency, the velocity data is aliased. Velocity information for a particular spatial location or a plurality of spatial locations (e.g. scan lines 11) is output. More than one signal sample may be provided for any given spatial location. For example, 1 to 12 samples are output for each spatial location. The velocity estimator 22 may also estimate energy and/or variance for each velocity estimate.

The velocity estimator 22 estimates multiple velocities from the received signals. For a spatial location, at least two velocities are estimated. One or more velocities are estimated from received signals for each pulse repetition interval. Different velocities for a same spatial location correspond to at least two different pulse repetition frequencies. The estimated velocities may or may not be aliased based on the actual velocity as compared to the pulse repetition frequency. Since velocities responsive to two or more pulse repetition intervals are estimated for the spatial locations, none, one, two, a subset, or all velocities may be aliased or not aliased.

The pulse repetition frequency may correspond to actual differences in transmission timing or differences in received signals selected for estimating the velocity. For example, the velocity estimator 22 selects the different subsets of signals for different pulse repetition intervals from signals acquired with a same transmission pulse repetition interval the memory 18. As another example, different velocities are estimated from different sets of received signals where each set is associated with a different transmitted pulse repetition frequency. Aliasing information associated with other non-transmitted pulse repetition frequencies may be derived from the received signals where multiple frequency pulses are transmitted. The filter 20 or another filter isolates information at two or more different frequencies for each set of signals. The velocity estimator 22 estimates velocities for each of the isolated sets of information.

The user input 26 is preferably a keyboard, buttons, joystick, trackball, mouse, sliders, touch pad, combinations thereof or other now known or later developed input device. The user input 26 provides signals to the processor 24 or other components of the system 10 in response to user activation. For example, the signals from the user input 26 control configuration of the system 10 for flow or tissue velocity imaging.

The processor 24 is preferably a digital signal processor, a general processor, an application specific integrated circuit, field programmable gate array, control processor, digital circuitry, analog circuitry, combinations thereof or other now known or later developed device for implementing calculations, algorithms, programming or other functions. The processor 24 operates pursuant to instruction provided in the memory 18 or a different memory.

Improving Frame Rate in Color Flow Ultrasound Imaging

Figure 3:
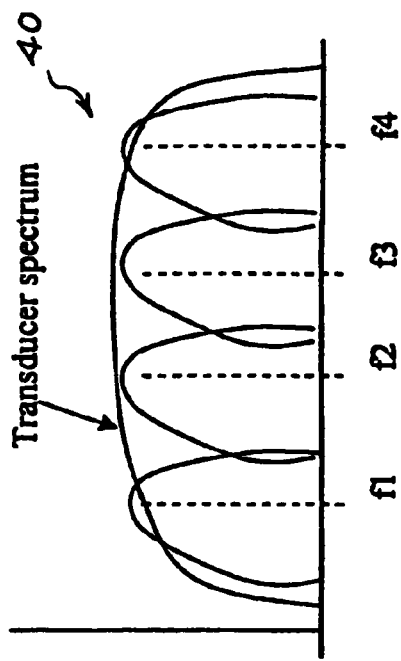
FIG. 3 is an illustration of the frequency spectrum of a preferred embodiment.
Figure 2:
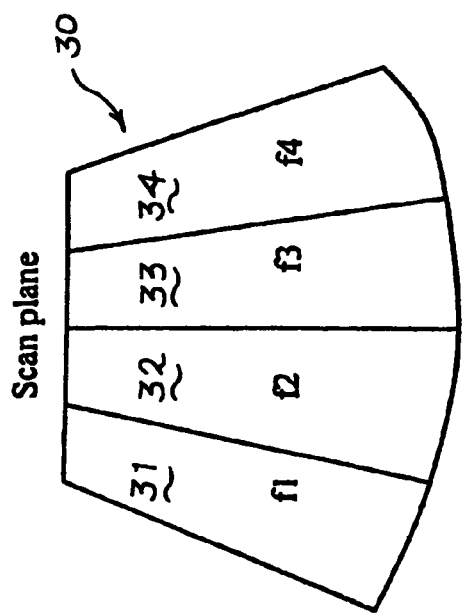
FIG. 2 is an illustration of a scan plane of a preferred embodiment in which a multi-beam transmit with different center frequencies is used at different spatial locations in the scan plane.

The system 10 of FIG. 1 can be used to improve frame rate in color flow ultrasound imaging. In one embodiment, the transmit beamformer 12 generates a plurality of transmit ultrasound beams. Each of the plurality of transmit ultrasound beams comprises a different center frequency and is directed at a different spatial location in the scan plane. It is preferred that multiple delay envelopes be used within a single transmit firing event in order to focus the beams in the different spatial locations. In the example shown in FIG. 2, the scan plan 30 is divided into four different spatial locations (spatial locations 31, 32, 33, and 34), and the transmit beamformer 12 generates four transmit ultrasound beams, one for each spatial location 31, 32, 33, and 34, at four different center frequencies (frequencies f1, f2, f3, and f4, respectively). As shown in the graph 40 in FIG. 3, the transducer spectrum comprises four frequency bands around the center frequencies f1, f2, f3, and f4 of the four transmit beams. Since each frequency band has very little overlap with an adjacent frequency band, each frequency band is virtually independent of the other, and, accordingly, very little interference exists between the frequency bands. Because of this, the four transmit ultrasound beams can be simultaneously generated, resulting in a frame rate improvement of 4X as compared to using a single beam with one center frequency. That is, if the scan plane comprises 128 lines, a transmit ultrasound beam of a given frequency would only be fired for 32 lines, as compared to 128 times if a single beam with one center frequency were used. Because the center frequencies of the four transmit beams are sufficiently far apart, the four transmit ultrasound beams can be simultaneously generated, resulting in four lines being fired instead of only one line being fired at any given time. It should be noted that while the frame rate improved by a factor of four in this example (because using four spatially distinct beams per transmit event results in a scan area for each frequency that is one-fourth of the total scan area), other unique multiple beam combinations are possible. The maximum number depends on the width of the transmit spectrum and the bandwidths used for the frequency bands as shown in FIG. 3. Additional information on ultrasound scanning using spatially- and spectrally-separated transmit ultrasound beams can be found in U.S. Pat. No. 6,159,153, which is hereby incorporated by reference.

Figure 4:
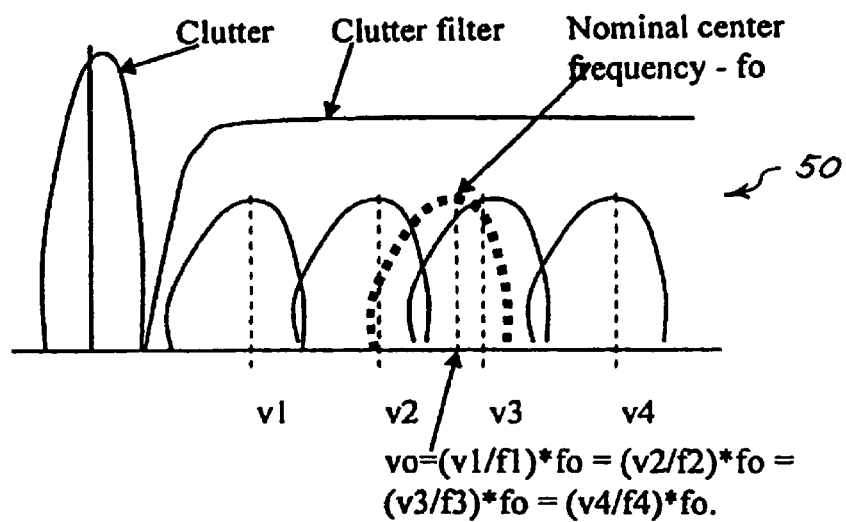
FIG. 4 is an illustration of velocity estimation for the illustration of FIG. 2.

After the transmit ultrasound beams are reflected by the subject undergoing examination, the receive beamformer 16 receives a plurality of receive ultrasound beams responsive to the plurality of transmit ultrasound beams. The system 10 then determines flow velocity, e.g., of blood flow within a vessel, based on the plurality of receive ultrasound beams. (As used herein, the terms flow velocity, velocity, and flow will be used interchangeably.) This is also known as Color Doppler Velocity, or "CDV." FIG. 4 is a graph 50, in the Doppler domain, of flow velocity in each of the spatial locations, with v1 corresponding to spatial location 31, v2 corresponding to spatial location 32, and so on, after demodulation. In addition to flow signals, there may exist signals from tissue and stationary targets called clutter. Because the tissue is stationary or slowly moving relative to the flow, the clutter appears as a low frequency shift. The clutter filter 28 (e.g., a high-pass filter), also known as a "wall filter," removes the contribution from stationary targets and tissue before estimating flow to best extract flow signals and to remove the velocity bias introduced by the clutter on the flow velocity.

Flow velocity depends on transmit frequency (flow velocity scales linearly with frequency) based on the Doppler principle. This can produce an anomaly. A constant flow of blood through a vessel in the whole scan plane can appear to be moving at different velocities in each spatial location 31, 32, 33, 34 when different frequencies f1, f2, f3, f4 from the locations 31, 32, 33, 34 are used due to different Doppler frequency shifts. Accordingly, in order to maintain velocity uniformity over the scan plane, it is preferred that, after flow velocity is estimated for each of the transmit frequencies, the velocity estimates of the different spatial locations be scaled according to some nominal center frequency (fo). In a presently preferred embodiment, this process involves: (1) demodulating the signals to the respective center frequencies (f1, f2, f3, f4), (2) obtaining velocity estimates (v1, v2, v3, v4) filtered around the center frequencies (f1, f2, f3, f4), and (3) obtaining velocities relative a nominal frequency fo according to the following formula: vo=v1/f1*fo=v2/f2*fo=v3/f3*fo=v4/f4*fo.

One advantage of this method is that it increases frame rate by at least a factor of two (because at least two different frequencies are used across the scan plane). In some high-end ultrasound platforms, the increase in frame rate can be by a factor of 16 (such as when a quad transmit beam and a quad receive beam for each transmit beam are used). This increase in frame rate can eliminate the need for the currently-used color pan box for traditional 2D imaging and in real-time 4D applications (i.e., 3D volumes over time).

To maintain uniform penetration and flow sensitivity in depth for all frequencies, coded excitation can be used for the higher frequencies. Coded excitation can include one or more of chirps, golay codes, barker codes, and other typically used coded pulse sequences. For uniformity in axial resolution, the absolute bandwidths at the different frequencies can be chosen to be similar to each other. Azimuthal video-filtering can be performed for the higher frequencies to obtain spatial uniformity over all azimuthal locations.

Figure 5:
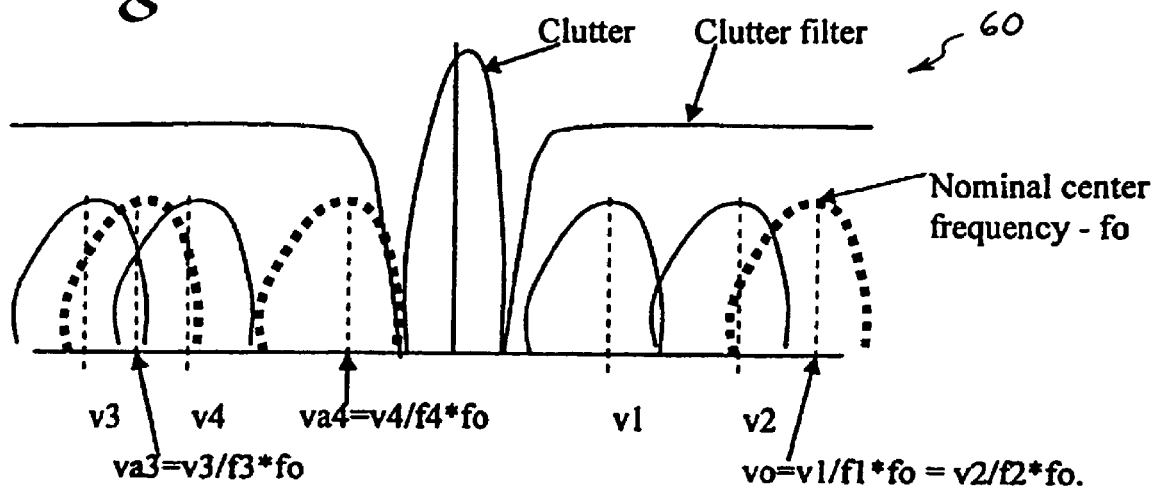
FIG. 5 is an illustration of an occurrence of aliasing for a uniform flow due to velocity estimation at different frequencies.

Flow velocity aliasing is possible if the pulse repetition interval ("PRI") is chosen too low As shown in graph 60 of FIG. 5, aliasing in the Doppler frequency domain for the example with unidirectional constant flow can occur since velocity estimation is derived from different frequencies. In general, with Doppler imaging, a pulse is transmitted every X microseconds to estimate flow at every point in the image. If the flow is too fast, the estimates will show the flow moving in the opposite direction (i.e., positive velocities become negative velocities because of aliasing). Accordingly, in FIG. 5, high frequencies produce high velocities, which can become negative velocities because of aliasing. In FIG. 5, the low frequency velocities (v1 and v2) are positive, and the high frequency velocities (v3 and v4) are negative. However, the high frequency velocities (v3 and v4) should also be positive because flow is in one direction. The high frequency velocities (v3 and v4) appear negative because of aliasing—sending in pulses at a given repetition frequency that is lower than the actual frequency that is needed for sampling. Because velocities v3 and v4 are negative, they cannot be scaled directly with velocities v1 and v2 using the technique described above. This is shown by the dotted-line curves va3 and va4 in FIG. 5.

Figure 6:
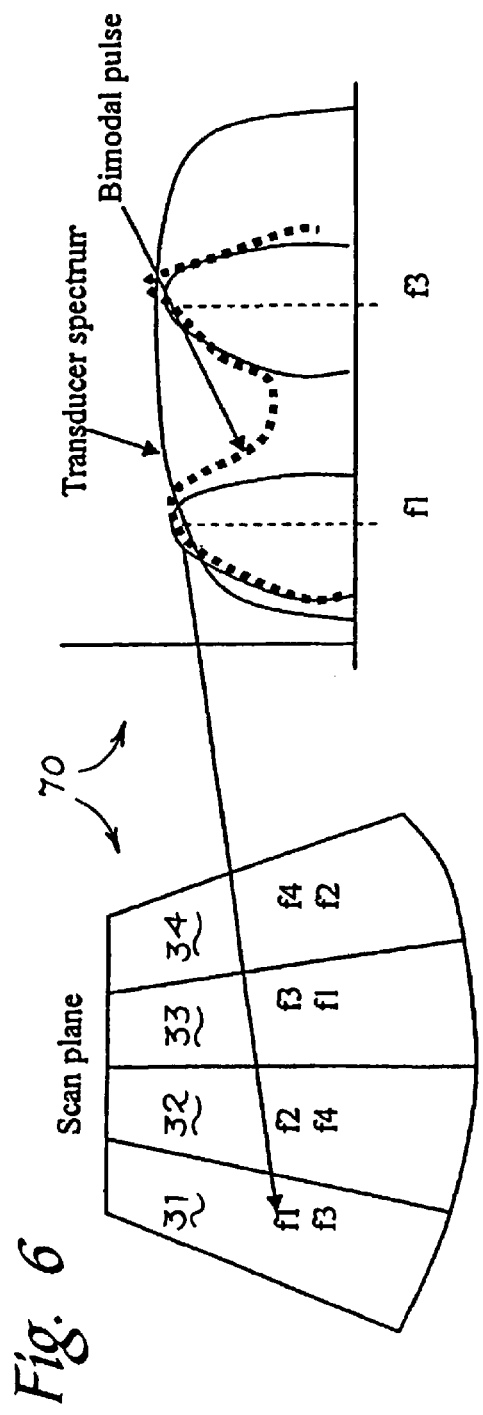
FIG. 6 is an illustration of a preferred embodiment of bimodal or multi-frequency transmit for frame-rate improvements in flow.

To reduce aliasing, it is preferred that a bimodal (or a multimodal) pulse or the superposition of two frequencies be used for each of the bands. This is shown in the graph 70 in FIG. 6, where there are two center frequency in each spatial location. For example, in spatial location 31, a bimodal pulse having center frequencies f1 and f3 is used. By using two frequencies in each spatial location, velocity can be estimated for each of the frequencies, and the frequency relationship between the estimates can be used to perform phase unwrapping (i.e., changing the phase) and, hence, reduce aliasing.

(U.S. patent application Ser. No. 10/458,156, the disclosure of which is incorporated by reference, discloses identification and setting of the pulse repetition frequency by unwrapping phase information.)

Figure 7:
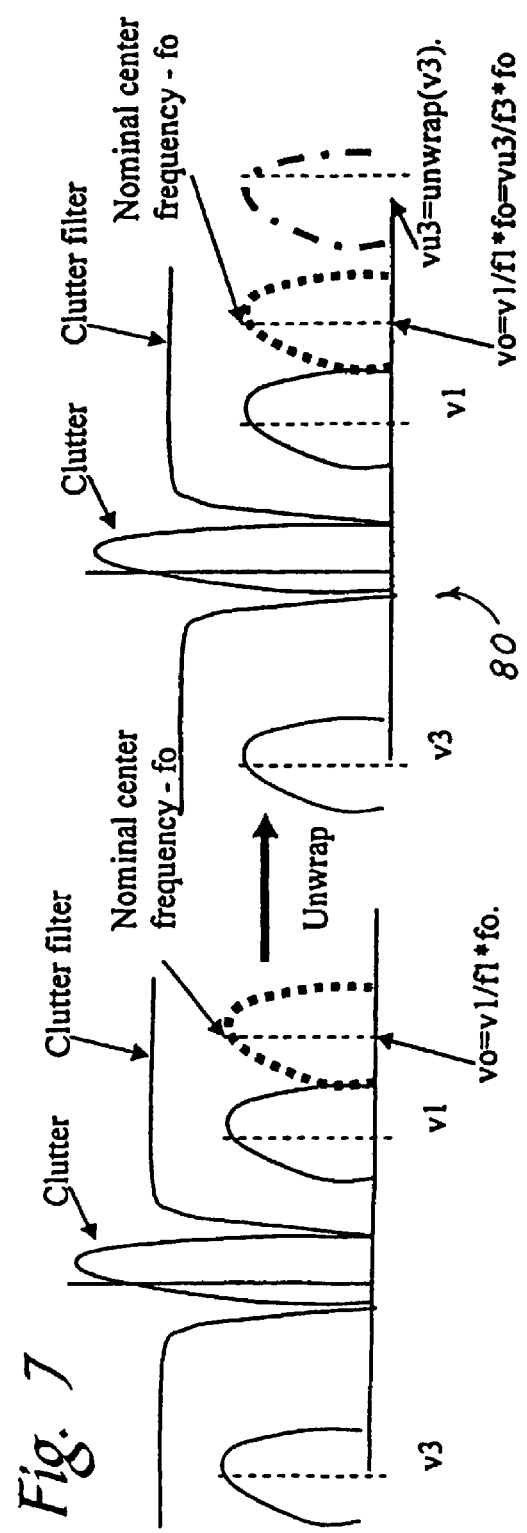
FIG. 7 is an illustration of a preferred embodiment showing the unwrapping procedure using a dual-frequency pulse or a bimodal pulse.

After unwrapping, velocity estimation at a nominal frequency is performed. FIG. 7 is an illustration 80 showing the unwrapping procedure using a dual-frequency pulse or a bimodal pulse. The following is a preferred algorithm for aliasing reduction using two frequencies f1 and f3 shown at the spatial locations 31 and 33 in FIG. 6 (illustration 70):

1) Demodulate by low freq (f1). Obtain velocity estimates (v1) after filtering around f1.
2) Demodulate by high freq (f3). Obtain velocity estimates (v3) after filtering around f3.
3) Replace low freq f1 estimates (v1) that have a insufficient signal strength or zero velocity, i.e. v1=0 and v3<>0, with v1=f1/f3*v3. (note: v3 could be aliased)
4) Replace high freq f3 estimates (v3) that have an insufficient signal strength or zero velocity, i.e. v3=0 and v1<>0, with v3=f3/f1*v1. (note: v1 could be aliased)
5) Compensate for aliased estimates as follows: If sign(v1) <>sign(v3) unwrap v3 according to
   a) if v3<0 then v3=v3+2*scale
   b) if v3>0 then v3=v3−2*scale.
6) Predict the high freq velocity estimates using the low velocity estimates and the frequency relationship (vp=v1*f3/f1).
7) Subtract the high freq estimates from the predicted (corrected) high frequency estimates (vp−v3).
8) Compensate for incorrect estimates as follows: if abs (vp−v3)>scale/threshold and
   a. if abs(v1)<abs(v3) then v3=v1*f3/f1;
   b. if abs(v1)>abs(v3) and if abs(v1)<scale/2 then v1=v3*f1/f3 else v3=v1*f3/f1. [threshold=1 usually]
   The threshold allows the degree of velocity correction for the low and high frequency estimates. Typically a threshold value of 1 is used.
9) Obtain the unaliased velocity estimate with respect to the nominal frequency fo as vo=(v1/f1*fo+v3/f3*fo)/2. If the velocity exceeds the scale then saturate the velocity estimate as follows.
   a. if vo>scale vo=scale;
   b. if vo<-scale vo=-scale;
10) Repeat steps 1 to 9 for the frequencies f2 and f4 for the spatial locations 32 and 34 in the schematic shown in FIG. 6 (illustration 70).

For illustration, consider a constant unidirectional flow, frequencies of f1=1, f2=1.5, f3=2, f4=3, a nominal frequency of 1.75 and a scale of 1.0. Some of the flow scenarios that are likely to occur during flow estimation are discussed below.

Case 1: all estimates are aliased; Let the estimated velocities before correction be v1=0.2, v2=0.3, v3=0.4, v4=0.6. For the nominal frequency fo=1.75, all estimates produce a velocity vo of 0.35;

Case 2: estimates at f1 and f2 are zero due to low Doppler frequencies suppressed by the stopband of the clutter filtering; Let the estimated velocities before correction be v1=0.0, v2=0.0, v3=0.2, v4=0.3. During correction, step 3 above results in nonzero estimates for f1 and f2 as v1=0.1 and v2=0.15. For the nominal frequency fo=1.75, all estimates produce a velocity vo of 0.175;

Case 3: estimates at f3 and f4 are aliased; Let the estimated velocities before correction be v1=0.5, v2=0.75, v3=1.0, v4=0.5 and vmax=1.0. During correction, step 5 above results in unaliased estimates for f3 and f4 as v3=1.0 and v4=1.5. For a nominal frequency fo=1.75, all estimates produce a velocity vo of 0.875;

Case 4: incorrect estimates at f3 and f4; Let the estimated velocities before correction be v1=0.5, v2=0.75, v3=0.0, v4=0.25 and vmax=1.0. During correction, step 4 results in velocity at f3 as v3=1.0, and step 6 results in predicted velocity at f4 as 1.5. For a threshold value of 1.0, step 8 results in corrected velocity estimate at f4 as v4=1.5. For the nominal frequency fo=1.75, all estimates produce a velocity vo of 0.875;

Case 5: all estimates are aliased; Let the estimated velocities before correction be v1=-1.0, v2=-0.5, v3=0.0, v4=1.0 and vmax=1.0. During correction, step 4 above results in corrected estimate at f3 as v3=-2.0. Step 5 results in unaliased estimate at f4 as v4=-1.0. For the nominal frequency fo=1.75, the estimates produced are therefore vo=-1.0 (at frequencies f1 and f3) and vo=-0.58 (at frequencies f2 and f4). Note that incorrect estimates are obtained for this case. It should be noted that, with the example above assuming four spatially distinct beams (others beam counts are possible), a factor of four improvement in frame rate is still possible assuming two identical pairs of dual frequency band pulses are sufficiently separated spatially. When there is insufficient spatial separation of beams that use identical frequency content, the frame rate improvement is only a factor of two compared to standard color flow imaging. Note that the aliasing reduction described above works for "mild" aliasing where the low frequency estimate has not aliased.

Figure 8:
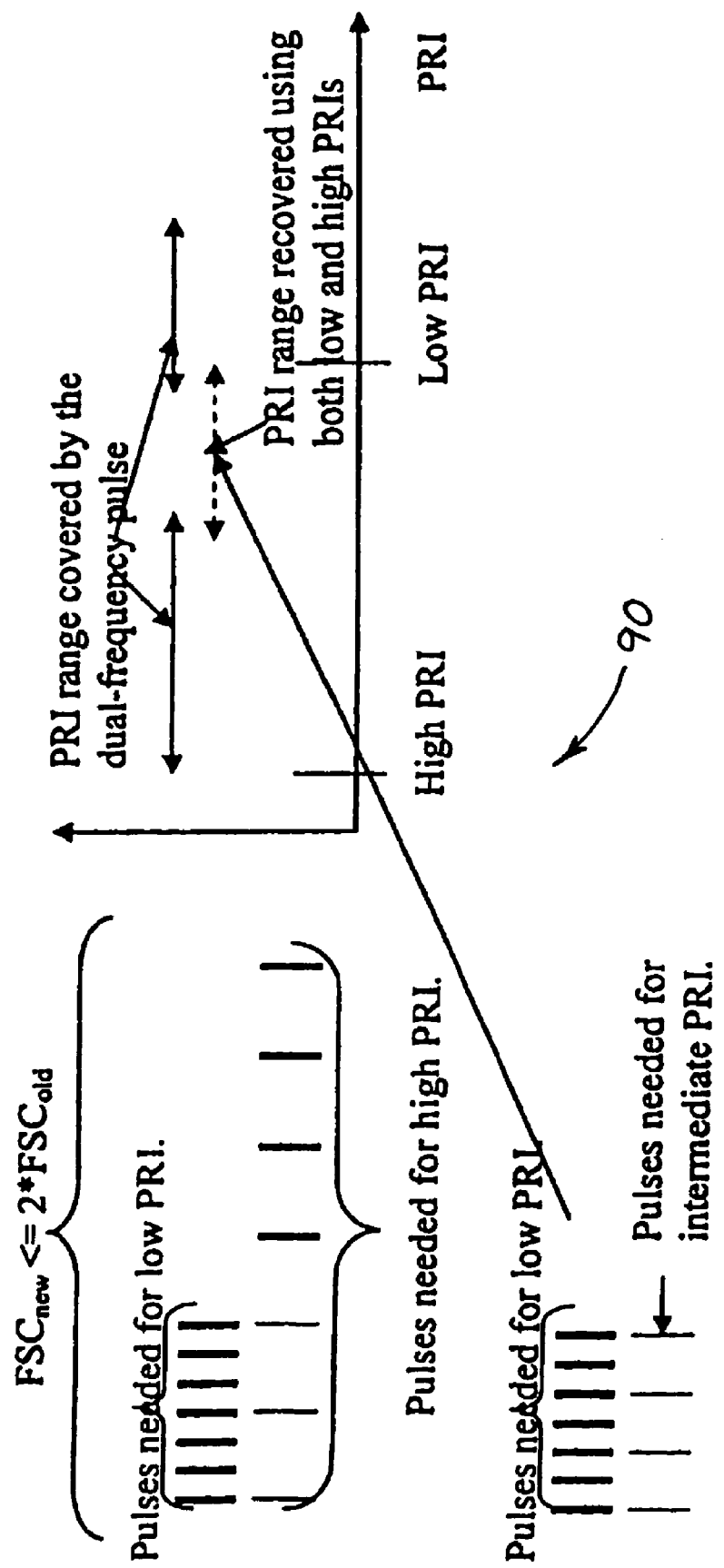
FIG. 8 is an illustration of a preferred embodiment of the flow sample count (FSC) for an aliasing reduction scheme.

To further reduce aliasing where more significant aliases occurs, a flow sample count ("FSC") with a low PRI as well as a high PRI can be used, as shown in the illustration 90 in FIG. 8. As shown in FIG. 8, flow estimates for some of the PRI settings that are intermediate between the low and high PRI settings can be obtained by skipping pulses in the FSC, re-estimating the flow using a shorter FSC, and using the velocity and PRI relationship appropriately. Note that this method results in a tradeoff between the frame-rate improvement and aliasing reduction described above since both the low and high PRIs use the same FSC as before so a larger effective FSC is used, reducing some of the earlier frame rate improvements.

In another embodiment, to improve the low-flow sensitivity, the same multimodal pulses are used as for the aliasing reduction method above. Where the estimate from the lower of two frequency bands in the bimodal pulse are rejected by the clutter filter or other filtering stages in the flow estimation process, the estimate from the higher of the two frequency bands in the bimodal pulse are used to fill pixel corresponding to the estimated spatial location.

Figure 9:
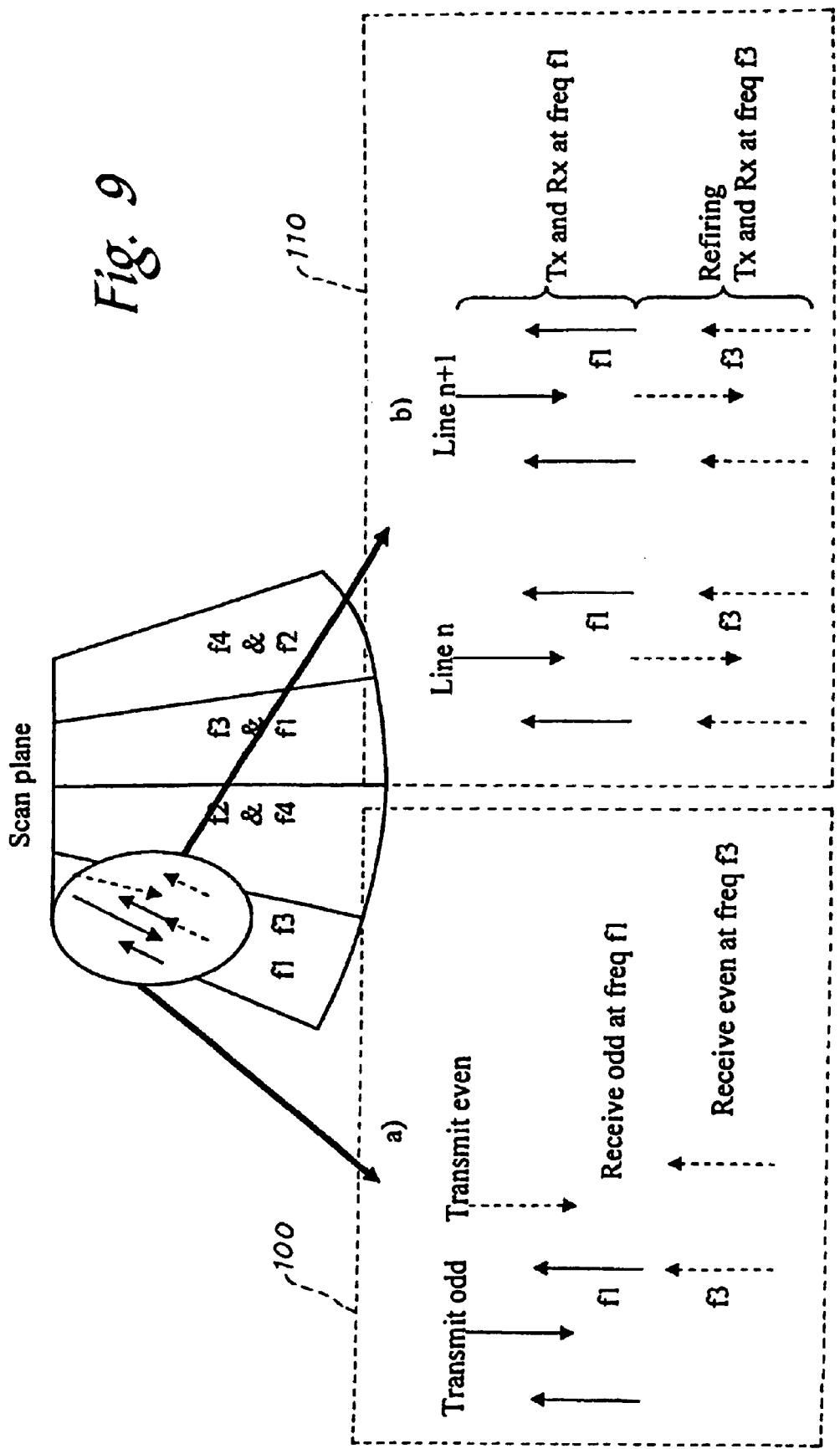
FIG. 9 is an illustration of a preferred embodiment showing alternating line frequencies for flow estimation, alternating line frequencies, and transmit refiring.

The multiple frequency methods proposed earlier such as bimodal pulses or chirps or coded waveforms sometimes might provide reduced flow sensitivity for applications that have thermal limitations. (U.S. Pat. No. 6,213,947 describes a medical diagnostic ultrasound imaging system using coded transmit pulses and is hereby incorporated by reference.) One alternate embodiment can be used to improve the sensitivity of flow estimation for thermally limited cases by using one frequency per transmit. The transmit scheme shown in the left-hand box 100 of FIG. 9 may be preferred for such cases. That transmit scheme alternates frequencies for each odd and even transmit beam along with a dual-beam receive. Since only one frequency is used per transmit, higher sensitivity relative to bimodal or coded pulses can be obtained for the same transmitted acoustic power. The dual frequencies for each receive line provides reduced aliasing and improved low flow sensitivity as explained earlier. Another alternative is shown in the right-hand box 110 of FIG. 9. In this alternative, transmit refiring scheme is used with a different frequency during refiring and the FSC is effectively repeated for each frequency. Flow is estimated separately for each frequency in the dual-beam. Note that the transmit line-spacing in the scheme shown in box 110 of FIG. 9 is twice that used in box 100 of FIG. 9 in order to obtain the same frame-rate. However, the spatial separation of the receive beams is the same for both cases. Alternative spatial separations are possible and produce different trade-offs in frame rates.

Figure 10:
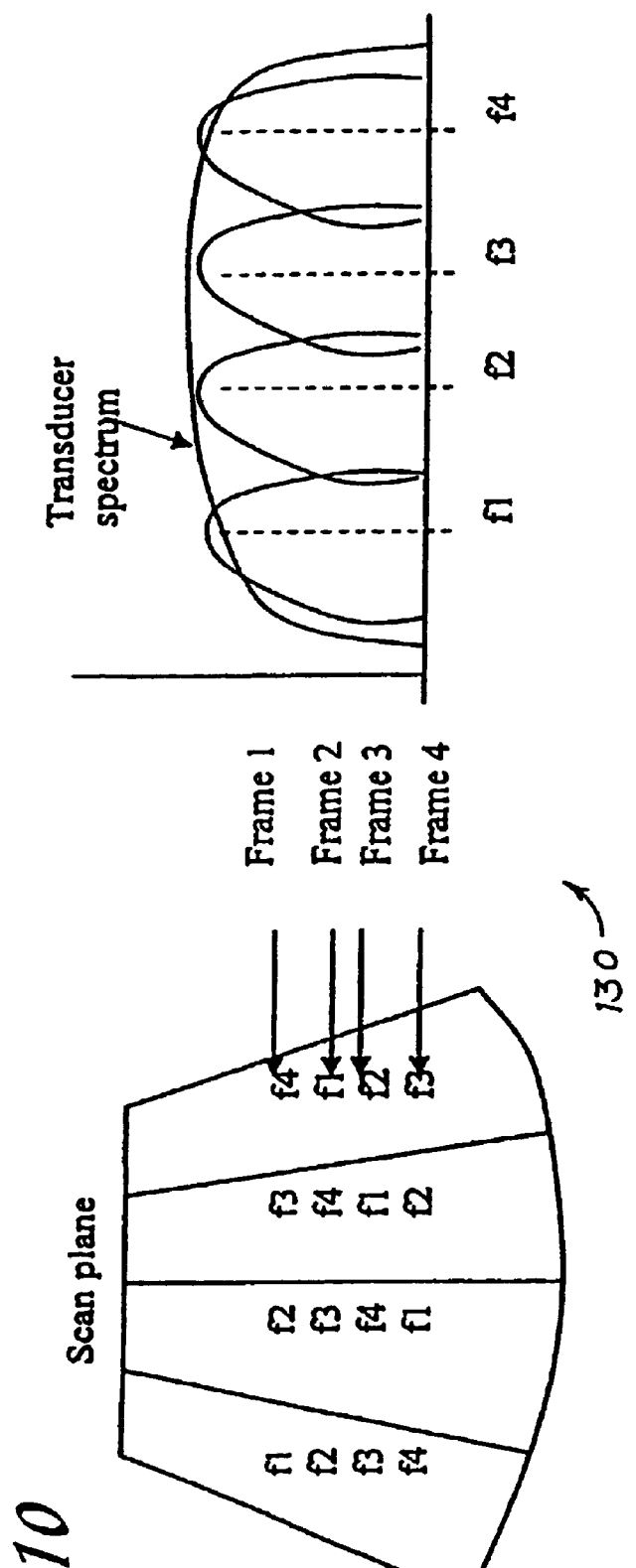
FIG. 10 is an illustration of a preferred embodiment showing interlacing and frame-persistence for variance reduction.

Alternatives can also be used to improve the signal-to-noise ratio ("SNR"). SNR improvement is feasible by averaging the estimates obtained from the multiple-frequencies at each location when multiple estimates are available. Frequency interlacing can also be used to improve SNR as follows. In this technique, the frequencies between frames are changed periodically as shown in the illustration 130 in FIG. 10. Averaging the estimates or persisting the flow estimates obtained at different frequencies results in a variance reduction and hence improved SNR. For each frame, the velocity estimate at a given spatial location from the previous frame is used for velocity antialiasing and low-velocity sensitivity improvement.

In an alternate embodiment, the user-interaction with the frequency selection control in color flow imaging is removed or minimized, when multiple frequency estimates are available, i.e. an automatic frequency selection mechanism is provided. When multiple frequency estimates are available, a nominal center frequency fo is used for scaling the estimates and providing one final estimate as explained earlier.

In an alternate embodiment, the user-interaction with the space-time (i.e. a control that allows a user trade-offs in spatial resolution and frame rate) selection is removed or minimized, i.e. an automatic space-time selection mechanism is provided. By increasing the azimuthal (and elevational in 3D) sampling during transmit, the spatial resolution is improved, however at the expense of frame-rate. Since, the frame-rate is improved when spatially distinct multiple frequencies are transmitted simultaneously, a trade-off between the frame-rate improvement and the spatial-resolution improvement occurs. An optimal setting based on such a trade-off can be determined a priori, and a single space-time selection that provides the best trade-off is chosen automatically.

In an alternate embodiment, the user-interaction with the filter selection is removed when multiple frequency estimates are available, i.e. an automatic filter selection mechanism is provided. Since dual-PRI along with the multiple frequencies is equivalent to providing a range of filters, the flow-estimation method automatically selects an appropriate filter from among those filters.

There are several advantages associated with these preferred embodiment. (1) As discussed above, frame-rate can be increased by at least a factor of 2, which may allow the removal of the color pan box and offer more practical volume flow imaging for 4D applications. (2) These preferred embodiments can provide robust flow estimation with low-flow sensitivity improvements, velocity aliasing reductions, and robustness with respect to minimizing PRI changes. (3) The preferred embodiments can provide simultaneous detection of high and low velocities without aliasing by trading off frame-rate with flow estimation using a larger FSC comprised of multiple PRIs. (4) Automatic PRI selections (i.e. scale selections) using at least two PRI settings upon activation is feasible with these embodiments without a reduction in the frame-rate. (5) These embodiments can provide a reduction in user-interactions with color controls like frequency, space-time (i.e. a control that allows trade-off in spatial resolution and temporal resolution), and filter. Controls like frequency and space-time can be eliminated or the user-interactions with those controls can be minimized since high frame-rates are obtained at all space-time and frequency settings. Similarly, the filter key can be removed since dual-PRI along with the multiple frequencies is equivalent to providing a range of filters, and the flow-estimation method automatically selects an appropriate filter from among those filters. (6) These preferred embodiments provide higher sensitivity for the same acoustic power transmission than pulse-compression methods when alternating line frequencies are used.

It is intended that the foregoing detailed description be understood as an illustration of selected forms that the invention can take and not as a definition of the invention. It is only the following claims, including all equivalents, that are intended to define the scope of this invention.

What is claimed is:

1. A method for improving frame rate in color flow ultrasound imaging, the method comprising:
   (a) generating a plurality of transmit ultrasound beams, each of the plurality of transmit ultrasound beams comprising a different center frequency and being directed at a different spatial location;
   (b) receiving a plurality of receive ultrasound beams responsive to the plurality of transmit ultrasound beams; and
   (c) determining flow velocity based on the plurality of receive ultrasound beams;
   wherein (c) comprises:
   estimating flow velocity for each of the center frequencies; and
   scaling the estimated flow velocities according to a nominal center frequency.

2. The method of claim 1, wherein (a) comprises using multiple delay envelopes for multiple transmit beams within a single transmit firing event.

3. The method of claim 1, wherein (c) comprises:
   demodulating each receive ultrasound beam to the center frequencies; and
   obtaining the velocity estimates after filtering for the center frequencies.

4. The method of claim 1, wherein coded excitation is used for a higher center frequency of the different center frequencies to obtain uniformity in penetration and sensitivity over all frequencies.

5. The method of claim 1, wherein azimuthal video-filtering is performed for a higher center frequency of the different center frequencies to obtain spatial uniformity.

6. The method of claim 1 further comprising reducing aliasing using multiple frequencies.

7. The method of claim 6, wherein each of the plurality of transmit ultrasound beams comprises at least two different center frequencies, and wherein aliasing is reduced by estimating flow velocity for each of the at least two different center frequencies and by using a frequency relationship between the estimates to perform phase unwrapping.

8. The method of claim 6, wherein aliasing is reduced by using a flow sample count with a low pulse repetition interval and a high pulse repetition interval where the high pulse repetition interval avoids aliasing.

9. The method of claim 8 further comprising obtaining flow estimates for at least one pulse repetition interval setting that is intermediate between a low and a high pulse repetition interval settings.

10. The method of claim 1 further comprising improving low-flow sensitivity.

11. The method of claim 10, wherein each of the plurality of transmit ultrasound beams comprises at least two different center frequencies, and wherein the low-flow sensitivity is improved by using an estimate from a higher of two frequency bands to fill pixels corresponding to an estimated spatial location where the lower frequency band estimate is insufficient.

12. The method of claim 1 further comprising alternating frequencies for odd and even transmit beams along with at least a dual-beam receive per transmit beam.

13. The method of claim 1 further comprising using a transmit refiring scheme with repeated flow sample count (FSC) at a different frequency.

14. The method of claim 1 further comprising improving signal-to-noise ratio by averaging estimates obtained from multiple frequencies at each location.

15. The method of claim 1 further comprising improving signal-to-noise ratio by frequency interlacing on a frame-by-frame basis.

16. The method of claim 1 further comprising an automatic selection of a user frequency control.

17. The method of claim 16, wherein the user frequency control comprises a frequency setting.

18. The method of claim 1 further comprising an automatic selection of a user space-time control.

19. The method of claim 18, wherein the user space-time control comprises a space-time setting.

20. The method of claim 1 further comprising an automatic selection of a user filter control.

21. The method of claim 20, wherein the user filter control comprises a filter setting.

22. A method for improving frame rate in color flow ultrasound imaging, the method comprising:
   (a) generating simultaneous spatially distinct transmit ultrasound beams with multiple frequency bands per transmit ultrasound beam;
   (b) estimating flow velocity for each frequency band of each transmit ultrasound beam; and
   (c) combining the flow velocity estimates at each spatial location.

23. The method of claim 22, wherein coded excitation is used for a higher frequency of the different frequency bands to obtain uniformity in penetration and sensitivity over all frequencies.

24. The method of claim 23, wherein aliasing is reduced by estimating flow velocity for each of the frequency bands and by using a frequency relationship between the estimates to perform phase unwrapping.

25. The method of claim 23, wherein aliasing is reduced by using a flow sample count with a low pulse repetition interval and a high pulse repetition interval where the high pulse repetition interval avoids aliasing.

26. The method of claim 22, wherein azimuthal video-filtering is performed for a higher frequency of the different frequency bands frequencies to obtain spatial uniformity.

27. The method of claim 22 further comprising reducing aliasing using estimates from the multiple frequency bands.

28. The method of claim 22 further comprising improving low-flow sensitivity.

29. The method of claim 22 further comprising alternating frequencies for odd and even transmit beams along with a dual-beam receive.

30. The method of claim 22 further comprising using a transmit refiring scheme with repeated FSC at a different frequency.

31. The method of claim 22 further comprising improving signal-to-noise ratio by averaging estimates obtained from multiple frequencies at each location.

32. The method of claim 22 further comprising improving signal-to-noise ratio by frequency interlacing on a frame-by-frame basis.

33. The method of claim 22 further comprising an automatic selection of the user a frequency control.

34. The method of claim 22 further comprising an automatic selection of the user a space-time control.

35. The method of claim 22 further comprising an automatic selection of a filter control.

36. A system for improving frame rate in color flow ultrasound imaging, the system comprising:
   a transmit beamformer configured to generate a plurality of transmit ultrasound beams, each of the plurality of transmit ultrasound beams comprising a different center frequency and being directed at a different spatial location;
   a receive beamformer configured to receive a plurality of receive ultrasound beams responsive to the plurality of transmit ultrasound beams; and
   a velocity estimator configured to determine flow velocity based on the plurality of receive ultrasound beams and a nominal center frequency.

37. The system of claim 36, wherein the transmit beamformer is configured to generate simultaneous spatially distinct transmit beams with multiple frequency bands per transmit beam, and wherein the velocity estimator is configured to estimate flow velocity for each frequency band and combine the flow velocity estimates at each spatial location.

38. The system of claim 36 further comprising a processor configured to reduce aliasing.

39. The system of claim 38, wherein the processor reduces aliasing by estimating flow velocity for each of the frequency bands and by using a frequency relationship between the estimates to perform phase unwrapping.

40. The system of claim 38, wherein the processor reduces aliasing by using a flow sample count with a low pulse repetition interval and a high pulse repetition interval.

41. The system of claim 36 further comprising a processor configured to improve low-flow sensitivity.

42. The system of claim 36, wherein the transmit beamformer alternates frequencies for odd and even transmit beams.

43. The system of claim 36, wherein the transmit beamformer uses a transmit refiring scheme with repeated FSC at a different frequency.

44. The system of claim 36, wherein the velocity estimator is configured to improve signal-to-noise ratio by averaging estimates obtained from multiple frequencies at each location.

45. The system of claim 36, wherein the velocity estimator is configured to improve signal-to-noise ratio by frequency interlacing on a frame-by-frame basis.

46. The method of claim 36 further comprising an automatic selection of a user frequency control.

47. The method of claim 46, wherein the user frequency control comprises a frequency setting.

48. The method of claim 36 further comprising an automatic selection of a user space-time control.

49. The method of claim 48, wherein the space-time control comprises a space-time setting.

50. The method of claim 36 further comprising an automatic selection of a user filter control.

51. The method of claim 50, wherein the user filter control comprises a filter setting.

* * * * *